United States Patent [19]

Huff et al.

[11] Patent Number: 4,686,226

[45] Date of Patent: Aug. 11, 1987

[54] SUBSTITUTED BENZO[B]FURO- AND BENZO[B]THIENO QUINOLIZINES

[75] Inventors: Joel R. Huff, Lederach; John J. Baldwin, Gwynedd Valley; Yojiro Sakurai, Lansdale; Joseph P. Vacca, Telford; James P. Guare, Jr., Quakertown, all of Pa.

[73] Assignee: Merck & Co., Inc., Rahway, N.J.

[21] Appl. No.: 771,927

[22] Filed: Sep. 3, 1985

[51] Int. Cl.$^4$ ............... C07D 491/497; C07D 495/14; A61K 31/38; A61K 31/435

[52] U.S. Cl. ..................................... 514/285; 546/62; 546/81; 546/82; 546/83; 546/89; 546/95; 546/80; 546/94

[58] Field of Search ................ 546/94, 95, 80, 81, 546/82, 62; 514/293, 285

[56] References Cited

U.S. PATENT DOCUMENTS

| | | | |
|---|---|---|---|
| 3,132,147 | 5/1964 | Schöpf et al. | 546/96 |
| 4,454,139 | 6/1984 | Ward et al. | 514/294 |
| 4,481,200 | 11/1984 | Ward et al. | 514/294 X |

FOREIGN PATENT DOCUMENTS

| | | | |
|---|---|---|---|
| 738420 | 7/1966 | Canada | 546/95 |
| 337846 | 6/1959 | Fed. Rep. of Germany | 546/95 |
| 1024902 | 4/1966 | United Kingdom | 546/95 |

OTHER PUBLICATIONS

Szantay et al., Chem. Abstracts, vol. 96 (1982), entry 6605e.

*Primary Examiner*—Nicholas S. Rizzo
*Assistant Examiner*—William A. Teoli, Jr.
*Attorney, Agent, or Firm*—William H. Nicholson; Michael C. Sudol

[57] ABSTRACT

Substituted hexahydro arylquinolizines and pharmaceutically acceptable salts thereof are selective $\alpha_2$-adrenergic receptor antagonists and thereby useful as antidepressants, antihypertensives, ocular antihypertensives, antidiabetics, antiobesity and platelet aggregation inhibitors and modifiers of gastrointestinal motility.

12 Claims, No Drawings

SUBSTITUTED BENZO[B]FURO- AND BENZO[B]THIENO QUINOLIZINES

BACKGROUND OF THE INVENTION

This invention is concerned with novel substituted hexahydro arylquinolizines or pharmaceutically acceptable salts thereof which are selective $\alpha_2$-adrenoceptor antagonists and are of value in conditions where selective antagonism of the $\alpha_2$-adrenoceptor is desirable for example as antidepressant, antihypertensive, ocular antihypertensive, antidiabetic, antiobesity agents, platelet aggregation inhibitors or modifiers of gastrointestinal motility. It also relates to processes for preparing the novel compounds, pharmaceutical compositions comprising the novel compounds and to a method of antagonizing $\alpha_2$-adrenoceptors.

The concept that the complex clinical state of depression is linked to a functional deficiency of monoamines in the central nervous system is now widely accepted. Numerous biochemical and clinical observations support the proposal that many forms of depressive illness are associated with reductions in adrenergic activity at functionally important sites in the brain. Thus, classical antidepressive drugs, such as amitriptyline and imipramine, are believed to act by blocking the neuronal reuptake of norepinephrine and/or serotonin, thereby enhancing the availability of the monoamines as neurotransmitters.

In addition to $\alpha_1$-adrenergic receptors which mediate postsynaptic responses to the neurotransmitter, norepinephrine, other adrenergic receptors are present at or near sympathetic terminals. These latter receptors, $\alpha_2$-adrenergic receptors, form part of a negative feedback system which modulates noradrenergic neurotransmission by controlling the impulse-induced release of norepinephrine from presynaptic terminals. Activation of $\alpha_2$-adrenergic receptors results in a decrease in the amount of norepinephrine normally released from the nerve terminals by nreve impulses while antagonism of $\alpha_2$-adrenergic receptors increases norepinephrine release. Therefore, molecules that block $\alpha_2$-adrenergic receptors afford an alternate approach to enhancement of noradrenergic function and the treatment of depression associated with an absolute or relative deficiency of adrenergic function.

$\alpha_2$-Adrenergic receptor antagonism is also associated with antidiabetic, antihypertensive, ocular antihypertensive, antiobesity, platelet aggregation inhibition activity, and modification of gastrointestinal motility.

Compounds structurally related to the novel compounds of this invention are disclosed in British Pat. Nos. 1,435,573 and 2,106,909 of John Wyeth and Brother, Ltd.

DETAILED DESCRIPTION OF THE INVENTION

This invention is concerned with a compound of structural formula I:

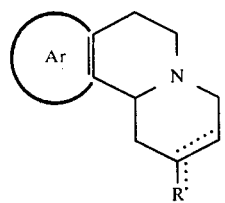

or a pharmaceutical acceptable salt thereof, wherein Ar represents an aromatic group such as:

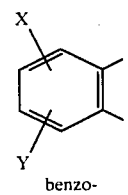
benzo-

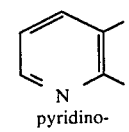
pyridino-

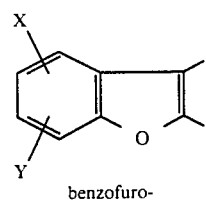
benzofuro-

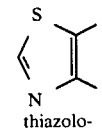
thiazolo-

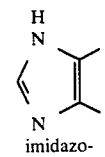
imidazo-

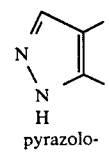
pyrazolo-

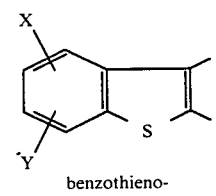
benzothieno-

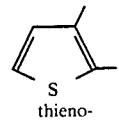
thieno-

-continued

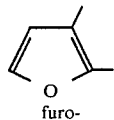
furo-

R is
(1) COOR$^1$ wherein R$^1$ is hydrogen or C$_{1-5}$ alkyl, either straight or branched chain;
(2)

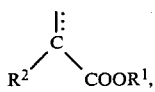

wherein R$^2$ is
(a) hydrogen,
(b) C$_{1-5}$ alkyl, or
(c) C$_{1-5}$ alkylidene;
(3)

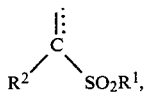

(4)

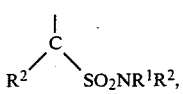

wherein R$^1$ and R$^2$ can be joined together to form a 5- or 6-membered heterocycle, such as pyrrolidino, morpholino, piperidino, or piperazino;
(5)

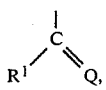

wherein Q is
(a) O, or
(b) N—OR$^1$;
(6)

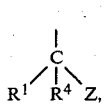

wherein Z is
(a) —OR$^3$ or —SR$^3$
(b) —NR$^2$R$^3$, wherein R$^3$ is
(i) H,
(ii) C$_{1-5}$ alkyl, unsubstituted or substituted with
(1) —OH,
(2) —COOR$^1$,
(3) —SO$_2$R$^2$,
(4) —N(R$^2$)SO$_2$R$^2$,
(iii) —COOR$^2$,
(iv) —SO$_2$R$^2$,
(v) —SO$_2$NR$^2$R$^3$; and R$^4$ is
(a) C$_{1-5}$ alkyl, or
(b) C$_{1-5}$ alkylidene; and
the broken lines represent possible double bonds.

The pharmaceutically acceptable salts coming within the purview of this invention include the pharmaceutically acceptable acid addition salts. Acids useful for preparing these acid addition salts include, inter alia, inorganic acids, such as the hydrohalic acids (e.g., hydrochloric and hydrobromic acid), sulfuric acid, nitric acidm abd phosphoric acid, and organic acids such as maleic, fumaric, tartaric, citric, acetic, benzoic, 2-acetoxybenzoic, salicyclic, succinic, theophylline, 8-chlorotheophylline, p-aminobenzoic, p-acetamidobenzoic, methanesulfonic, or ethanedisulfonic acid.

The novel compounds of this invention wherein R is attached by a single bond are depicted herein as having the configuration in which the hydrogen at C-12b and R at C-2 are trans

and it is more preferred diastereomer for $\alpha_2$-adrenoceptor blockade activity. However, the isomers having the configuration in which the hydrogen at C-12b and R at C-2 are cis are also active $\alpha_2$-adrenoceptor blockers and are considered to be within the scope of this invention. Each of the 2RS,12bSR and 2RS,12bRS-configurational isomers are racemates capable of being resolved into dextrorotatory and levorotatory enantiomers. This invention includes these pure enantiomers as well as all mixtures thereof, especially the racemates. However, the (12bS)-enantiomer is preferred.

It is also preferred that Ar be X,Y-benzo, X,Y-benzo[b]furo; or X,Y-benzo[b]thieno-. It is even more preferred that Ar be benzo[b]furo.

It is further preferred that R be $$\overset{|}{C}H_2CO_2R^1 \text{ or } CH_3\overset{|}{\underset{|}{C}}CO_2R^1$$

wherein R$^1$ is C$_{1-5}$ alkyl;

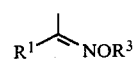

wherein R$^1$ and R$^3$ are independently C$_{1-5}$ alkyl;

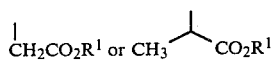

wherein R$^1$ and R$^4$ are C$_{1-5}$ alkyl or hydrogen. It is most preferred that R$^1$, R$^3$ and R$^4$ in each of the above is methyl.

For those compounds wherein R is

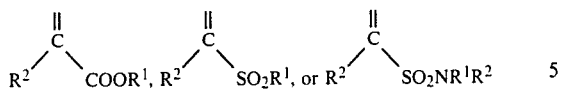 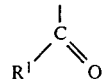

the synthesis comprises treating the 2-oxo-quinolizine with the appropriate Wittig reagent in the presence of a strong base such as KH or n-butyl lithium in an inert aprotic solvent such as an ether, for example, THF, diethyl ether, glyme, tetrahydropyran or the like in an inert atmosphere at about −70° C. to 0° C. for about 0.5 to about 3 hours followed by spontaneous warming to room temperature over about 16 hours.

The above compounds are readily reduced to form the saturated analogs with palladium on carbon, platinum oxide or other noble metal catalyst in a lower alkanol at about 40 psi of hydrogen until the requisite amount of hydrogen is absorbed; usually about 0.5 to about 3 hours.

The novel compounds wherein R is —COOR$^1$ are produced in accordance with the following reaction scheme:

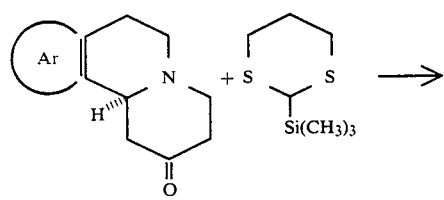

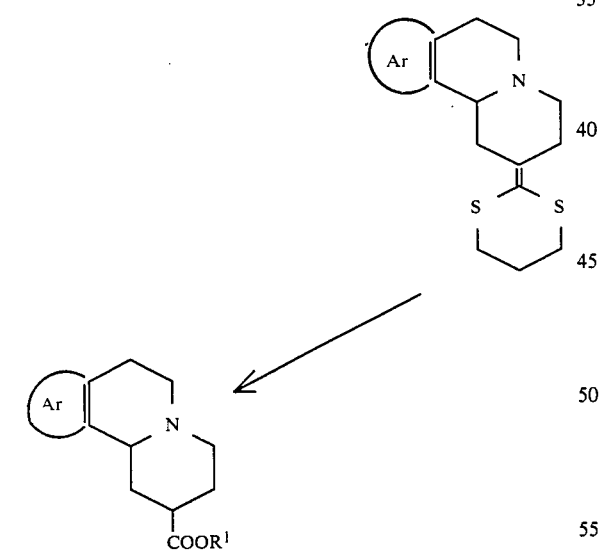

The reaction with the 2-trimethylsilyl-1,3-dithiane is conducted in an ethereal solvent such as THF, tetrahydropyran, or diethyl ether in the presence of a strong base such as potassium or sodium hydride, or a metal organic such as n-butyl lithium, at about, −40° C. to −10° C. followed by spontaneous warming to room temperature. After isolation of the 1,3-dithian-2-ylidene derivative it is treated with a lower alkanol, such as ethanol, saturated with hydrogen chloride at about 25° to 75° C. for about 1 to 5 hours.

Compounds wherein R is

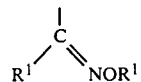

are prepared by treating the 2-oxoquinolizine with 1-ethylthiotri(alkyl)phosphonate under Wittig conditions as described above. The reaction mixture is then treated with water and saturated aqueous ammonium chloride solution to generate the 1-oxoalkane or alkanoyl substituent.

The oximes, i.e. R is

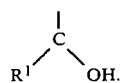

are readily prepared from the alkanoyl derivatives by treatment with hydroxylamine or alkoxyamine in an organic base such as pyridine, optionally diluted with a loweralkanol such as ethanol.

Reduction of the 2-alkanoyl compounds with a complex metal hydride such as lithium aluminum hydride in an ethereal solvent at bout −10° C. to about +30° C. produces the compounds wherein R is

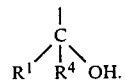

Treatment of the 2-alkanoyl compouds with a Grignard reagent such as R$^4$MgBr at about −10° C. to +10° C. in an ethereal solvent for about 1 to 4 hours provides the compounds wherein R is

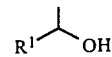

Treatment of the compounds wherein R is

R$^1$—C(OH)— with sodium or potassium hydride or phenyl lithium followed by ethyl bromoacetate provides the ethoxycarbonylmethyl ether which on reduction with sodium borohydride provides the compounds wherein R is

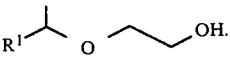

The condensation with ethyl bromoacetate is conducted at about −10° to +10° C., preferably 0° C. in an inert protic solvent such as a benzene/DMF mixture over a period of about 1 to 5 hours. The borohydride reduction is conducted in refluxing t-butanol for about 0.5 to 2 hours.

Compounds wherein R is

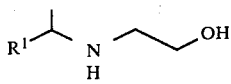

are prepared by treatment of a 2-alkanoylquinolizine

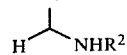

are prepared in accordance with the following reaction scheme:

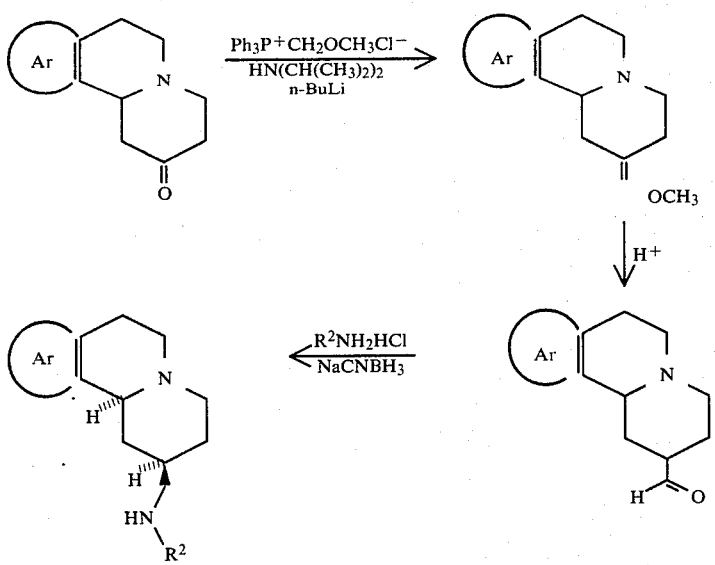

with ethanolamine and sodium cyanoborohydride (NaCNBH$_3$) in methanolic hydrogen chloride at about 15° to 30° C. over a period of about 10 to 30 hours.

Compounds wherein R is

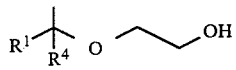

are most readily prepared by preparing the ethylene ketal of the 2-alkanoyl-quinolizine by treating the alkanoyl compound with ethylene glycol, followed by treatment of the ketal with a Grignard reagent of formula R$^4$MgBr. The ethylene ketal is formed by treating a mixture of the ethylene glycol and the 2-alkanoyl-quinolizine with boron trifluoride etherate in a chlorinated alkane such as methylene chloride, chloroform or the like at about 15° to 35° C. for about 10 to 24 hours in the absence of light. The Grignard reaction is conducted in an aromatic hydrocarbon such as benzene, toluene or the like at about 70°–90° C., conveniently in refluxing benzene.

If the hemithioketal prepared with 2-mercaptoethanol as described above for preparation of the ethylene ketal is added to a cold (0° C.) solution of aluminum chloride and lithium aluminum hydride in ether followed by refluxing for 2 hours followed by acidification, there are produced the compounds wherein R is

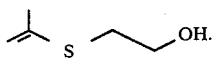

Compounds wherein R is

The first step, or Wittig reaction is conducted in an ethereal solvent such as THF, diethyl ether, glyme, tetrahydropyran or the like in an aromatic solvent such as benzene, toluene or the like at about −10° to +5° C. over about 0.5 to 2 hours. Hydrolysis of the enol ether is accomplished by treatment with dilute mineral acid such as hydrochloric acid at about room temperature, although the temperature is not critical. The resulting formyl compound is then reductively aminated with R$^2$NH$_2$.HCl and sodium cyanoborohydride as described above for preparation of compounds with R=

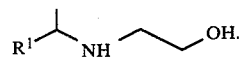

Treatment of the HNHR$^2$ derivative with an acid chloride such as R$^2$R$^3$NSO$_2$Cl in the presence of an acid acceptor such as triethylamine in an inert solvent at about 10° to 40° C. for 10 to 24 hours produces the compounds wherein R is

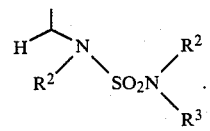

In the novel method of treating depression, ocular hypertension, hypertension, diabetes, obesity or platelet aggregation, or modifying gastrointestinal motility, a novel compound or pharmaceutically acceptable salt thereof, is administered in an amount ranging from about 0.01 to about 20 mg per kg of body weight per day, preferably from about 0.1 to about 10 mg per kg of body weight per day in a single dose or in 2 to 4 divided doses.

For the treatment of depression the novel compounds of this invention can be administered as the sole active ingredient or in combination with other antidepressants such as amitriptyline, imipramine or other norepipherrine or serotonin reuptake inhibitor or a monoamine oxidase inhibitor.

The compounds, or pharmaceutically acceptable salts thereof, of the present invention, in the described dosages, are administered orally, intraperitoneally, subcutaneously, intramuscularly, transdermally or intravenously. They are preferably administered orally, for example in the form of tablets, troches, capsules, elixirs, suspensions, syrups, wafers, chewing gum, or the like prepared by art recognized procedures. The amount of active compound in such therapeutically useful compositions or preparations is such that a suitable dosage will be obtained.

EXAMPLE 1

(2RS,12bSR)-Methyl (1,3,4,6,7,12b-hexahydro-2H-benzo[b]furo[2,3-a]quinolizin-2-yl)acetate Hydrochloride Step A: Preparation of 3-Cyanomethylbanzo[b]furan To a suspension of 2.64 gms (0.11 mole) of oil free sodium hydride in 200 mL of tetrahydrofuran (THF) were added dropwise a solution of 19.47 gms (0.11 mole) of diethylcyanomethylphosphonate in 75 mL of THF. After the $H_2$ evolution has ceased, a solution of 13.4 g (0.1 mole) of 3-(2H)-benzo[b]furanone in 100 mL of THF was added. The solution was heated at 70° C. for 1.5 hrs, cooled, and poured into 500 mL of 5% HCl, and washed with ether. The ether phase was washed with brine, dried ($MgSO_4$), filtered and concentrated to give 15.4 g of a dark oil. The product was distilled at 96°–100° C./0.075 mm Hg to give 10.85 g of a yellow oil which crystallized upon standing.

Step B: Preparation of 2-(3-benzo[b]furanyl)ethylamine

A solution of 3.97 g (0.025 mole) of 3-cyanomethylbenzo[b]furan in 200 mL of diethyl ether was slowly added to a refluxing suspension of 3.84 g (0.1 mole) of lithium aluminum hydride in 400 mL of ether. The reaction was heated 3 hrs., cooled and water was slowly added. The suspension was filtered through a pad of filter aid and the filtrate was evaporated to give 3.2 g of oily product. The hydrochloride salt has m.p. 183°–185° C.

Step C: Preparation of 3-(2-Formamidoethyl)benzo[b]furan

A solution of 2.35 g (0.015 mole) of 2-(3-benzo[b]furanyl)ethylamine and 5 mL of ethyl formate was heated at 60° C. for 3 hours, poured into 2N HCl and washed with methylene chloride which in turn was washed with 5% sodium hydroxide (w/v), dried ($MgSO_4$), filtered and concentrated to give 2.70 g of product.

Step D: Preparation of 3,4-dihydrobenzo[b]furo[2,3-c]pyridine 2.28 Grams (0.012 mole) of 3-(2-formamidoethyl)benzo[b]furan was added to 28 g of polyphosphoric acid which was preheated to 100° C. After 1–1.5 hours, the reaction mixture was poured onto ice and the residues were washed with water. The polyphosphoric acid was dissolved in water, filtered through a pad of celite and made basic with concentrated ammonia. A precipitate was collected and dried to give 1.45 g of product, m.p. 170°–171° C.

Step E: Preparation of (12bRS)-1,3,4,6,7,12b-Hexahydrobenzo[b]furo[2,3-a]quinolizin-2-one To a solution of 12 g (0.070 mol) of 3,4-dihydrobenzo[b]furo[2,3-c]pyridine dissolved in 500 mL of acetonitrile at 60° C. was added 20 g (0.140 mol) of 2-trimethylsiloxy-1,3-butadiene followed by 13.6 g (0.10 mol) of anhydrous zinc chloride. The mixture was heated at 60° C. for 1.5 hour, cooled to 25° C., and 30 mL of 5% HCl was added and stirred 10 minutes. 40% Sodium hydroxide was added until the reaction was basic; 200 mL of water added; and the acetonitrile layer was separated. The aqueous layer was filtered through celite and washed with ether. The combined organic layers were dried ($Na_2SO_4$), filtered, and concentrated to a brown residue which was chromatographed (silica, ethyl acetate/hexane (1:1)) to give 8.2 g of product, m.p. 108°–9° C.

Resolution of (12bSR)-1,3,4,6,7,12b-hexahydrobenzo[b]furo[2,3-a]quinolizin-2-one A solution of (−)-di-p-toluoyl-L-tartaric acid monohydrate (25.9 g) in 100 mL of ethyl acetate was mixed with a solution of (12bSR)-1,3,4,6,7,12b-hexahydrobenzo[b]furo[2,3-a]quinolizin-2-one (15.5 g) in 700 mL of ethyl acetate and allowed to stand 12–78 hours. The mixture was filtered to yield 21 g of the di-p-toluoyl-L-tartrate salt of the amine. The free base was liberated by partitioning between aqueous $Na_2CO_3$ and ethyl acetate ($[\alpha]_D$=ca. −79°; C=0.001; $CHCl_3$). The diastereomeric salt of this material was again prepared following the above procedure. The collected di-p-toluoyl-L-tartrate salt was partitioned between ethyl acetate and aqueous $Na_2CO_3$, dried ($Na_2SO_4$), filtered, treated with charcoal, filtered and evaporated to yield 5.4 g (35%) of (12bS)-1,3,4,6,7,12b-hexahydrobenzo[b]furo[2,3-a]quinolizin-2-one; $[\alpha]_D$=−84°; (C=0.001, $CHCl_3$).

The (12bR)-1,3,4,6,7,12b-hexahydrobenzo[b]furo[2,3-a]quinolizin-2-one was obtained by substituting (+)-di-p-toluoyl-D-tartaric acid monohydrate for (−)-di-p-toluoyl-L-tartaric acid in the above procedure to provide product with $[\alpha]_D$=+84° (C=0.001, $CHCl_3$).

Step F: Preparation of E and Z Methyl (1,3,4,6,7,12b-hexahydro-2H-benzo[b]furo[2,3-a]quinolizin-2-ylidene) acetate Hydrochloride Trimethyl phosphonoacetate (728 mg; 4 mmol) in 2 mL of dry THF was added to a suspension of KH (668 mg of a 24% oil dispersion; 4 mmol) in 2 mL of dry THF at 0° C. under an atmosphere of nitrogen. After 30 minutes at 0° C., 1,3,4,6,7,12b-hexahydro-2H-benzo[b]furo[2,3-a]quinolizin-2-one (241 mg; 1 mmol) was added, and the reaction mixture was stirred at room temperature for 18 hours. The mixture was partitioned between $CH_2Cl_2$ and water. The organic layer was separated and evaporated to an oil which was chromatographed over silica gel, eluting with 15% ethyl acetate/hexane. The E olefin (110 mg) and Z olefin (100 mg) were obtained as oils which were converted to HCl salts melting at 218°–219° C. and 220°–221° C. respectively.

Step G: Preparation of (2RS,12bSR)-Methyl (1,3,4,6,7,12b-hexahydro-2H-benzo[b]furo[2,3-a]quinolizin-2-yl) acetate Hydrochloride A 1:1 mixture of the E and Z olefins from Step A (700 mg) and 10% Pd on carbon (75 mg) in 100 mL of ethanol were hydrogenated at 40 psi (2.8×10⁵ Pa) for 1.5 hours. After separating the catalyst by filtration, the filtrate was evaporated to dryness. The resulting oil was chromatographed over silica gel, eluting with 40% ethyl acetate/hexane. The product was collected as an oil (370 mg) which crystallized upon standing. The free base was converted to the HCl salt, m.p. 194°–195° C.

Starting with optically active 1,3,4,6,7,12b-hexahydro-2H-benzo[b]furo[2,3-a]quinolizin-2-one and employing the procedures in Steps A and B, the enantiomerically pure products are obtained.

EXAMPLE 2

(2RS,12bSR,2'RS) and (2RS,12bSR,2'SR)-Ethyl 2'-(1,3,4,6,7,12b-hexahydro-2H-benzo[b]furo[2,3-a]quinolizin-2-yl) propionate Hydrochloride

Step A: Preparation of E and Z Ethyl 2'-(1,3,4,6,7,12b-hexahydro-2H-benzo[b]furo[2,3-a]quinolizin-2-ylidene) propionate Employing the procedure described in Step F of Example 1, and substituting triethyl 2-phosphonopropionate for trimethyl phosphonoacetate, the product was obtained as a mixture of E and Z geometric isomers which were separated by chromatography over silica gel, eluting with 20% ethyl acetate/hexane.

Step B: Preparation of (2RS,12bSR,2'RS)-Ethyl 2'-(1,3,4,6,7,12b-hexahydro-2H-benzo[b]furo[2,3-a]quinolizin-2-yl) propionate Hydrochloride Hydrogenation of the Z olefin (150 mg) obtained in Step A according to the procedure described in Step G of Example 1 yielded the free base of the product (100 mg) after chromatography over silica gel, eluting with 20% ethyl acetate/hexane. Conversion of the free base to the HCl salt afforded a white crystalline material, m.p. 251°–252° C.

Step C: Preparation of (2RS,12bSR,2'SR)-Ethyl 2'-(1,3,4,6,7,12b-hexahydro-2H-benzo[b]furo[2,3-a]quinolizin-2-yl) propionate Hydrochloride The E olefin (200 mg) obtained in Step A and 50 mg PtO₂ in 50 mL of ethanol was hydrogenated at 40 psi (2.8×10⁵ Pa) for 18 hours. The catalyst was filtered, and the solvent was evaporated. The resultant oil was chromatographed over silica gel, eluting with 20% ethyl acetate/hexane to afford the free base of the product. The free base was converted to the HCl salt, m.p. 188°–191° C.

Employing the procedure substantially as described in Examples 1 and 2 but substituting for the Wittig reagents and the benzo[b]furoquinolizin-2-ones used therein, the Wittig reagents and arylquinolizin-2-ones described in Table I there are prepared the acetic acid esters also described in Table I, in accordance with the following reaction scheme:

TABLE I

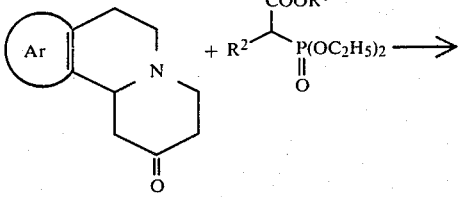

| Ar | R² | R¹ |
|---|---|---|
| benzo- | H | —C₂H₅ |
| benzo[b]thieno- | —CH₃ | —CH₃ |
| thieno- | —CH(CH₃)₂ | —(CH₂)₂CH₃ |
| furo- | —CH₂—CH=CH₂ | —C₄H₉ |

EXAMPLE 3

E and Z 2-(1-Ethylsulfonylethylidene)-1,3,4,6,7,12b-hexahydro-2H-benzo[b]furo[2,3-a]quinolizine Hydrochloride and 2-(1-Ethylsulfonylethyl)-1,6,7,12b-tetrahydro-3H-benzo[b]furo[2,3-a]quinolizine Hydrochloride α-Diethylphosphonoethylsulfone (1.34 g; 5.2 mmol) was dissolved in 20 mL of THF and cooled to −70° C. under N₂ gas. To this solution, n-butyl lithium was added dropwise, and the mixture was stirred for 1 hour. 1,3,4,6,7,12b-Hexahydro-2H-benzo[b]furo[2,3-a]quinolizin-2-one (0.96 g; 4 mmol) in 10 mL of THF was added at −70° C. under N₂ gas, and the reaction mixture was heated at 50° C. overnight. A saturated NH₄Cl solution and ether were added to the reaction mixture, and the ether layer was separated, washed with H₂O, dried over MgSO₄, and evaporated to give an oil. The free base of the products were separated by chromatography over silica gel, eluting with 12% ethyl acetate/CH₂Cl₂ and converted to HCl salts to give: Z-2-(1-Ethylsulfonylethylidene)-1,3,4,6,7,12b-hexahydro-2H-benzo[b]furo[2,3-a]quinolizine Hydrochloride m.p. 210°–212° C.; E-2-(1-Ethylsulfonylethylidene)-1,3,4,6,7,12b-hexahydro-2H-benzo[b]furo[2,3-a]quinolizine Hydrochloride m.p. 247°–248° C.; and 2-(1-Ethylsulfonylethyl)-1,6,7,12b-tetrahydro-3H-benzo[b]furo[2,3-a]quinolizine Hydrochloride m.p. 222°–223° C.

EXAMPLE 4

(2RS,12bSR)-Ethyl 1,3,4,6,7,12b-Hexahydro-2H-benzo[b]furo[2,3-a]quinolizine-2-carboxylate Hydrochloride

Step A: Preparation of (12bSR)-2-(1,3-dithian-2-ylidene)-1,3,4,6,7,12b-hexahydrobenzo[b]furo[2,3-a]quinolizine 2-Trimethylsilyl-1,3-dithiane (0.77 g; 4 mmol) was dissolved in 10 mL dry THF and cooled to −25° C. with a dry ice/CCl₄ bath. To this was added 1.6 ml n-butyl lithium (1.6M solution in hexane) and the solution was stirred for 2 hours at −25° C., after which time 0.422 g (1.75 mmol) (12bRS)-1,3,4,6,7,12b-hexahydro-2H-benzofuro[2,3-a]quinolizin-2-one was added and the reaction mixture was allowed to warm to room temperature (15 minutes). The reaction mixture was poured into 50 mL H₂O and extracted with 3×25 mL CH₂Cl₂. The combined organics were extracted with 5×20 mL H₂O, 1×25 mL brine, dried (MgSO₄) and the solvent was removed in vacuo. Purification by medium pressure chromatography (CHCl₃) yielded 0.385 g (64%) product as a yellow crystalline solid, m.p. 133°–134° C.

Step B: Preparation of (2RS,12bSR)-Ethyl 1,3,4,6,7,12b-hexahydro-2H-benzo[b]furo[2,3-a]quinolizine-2-carboxylate Hydrochloride (12bSR)-2-(1,3-Dithian-2-ylidinyl)-1,3,4,6,7,12b-hexahydrobenzo[b]furo[2,3-a]quinolizine (0.18 g; 0.524 mmol) was dissolved in 30 mL absolute ethanol which previously had been saturated with HCl gas. The reaction was heated to 50° C. for 3 hours, the solvent was removed and the residue was partitioned between 25 mL ethyl acetate and 25 mL 20% NaOH solution. The aqueous layer was separated and the organic layer washed with 1×20 mL 20% NaOH, 3×25 mL H₂O, 1×25 mL brine, dried (MgSO₄) and the solvent was removed in vacuo. Purification by spinning disc chromatography (1% methanol/CHCl₃) yielded 0.12 g (77%) of the product as an oil. The oil was dissolved in 20 mL ethyl acetate and ethanolic HCl was added to give a white solid, m.p. 228°–230° C. (dec).

Employing the procedure substantially as described in Example 4, Step B, but substituting for the ethanol reagent used therein comparable amounts of an alcohol of structure R¹OH, there are produced the esters described below in accordance with the following reaction scheme:

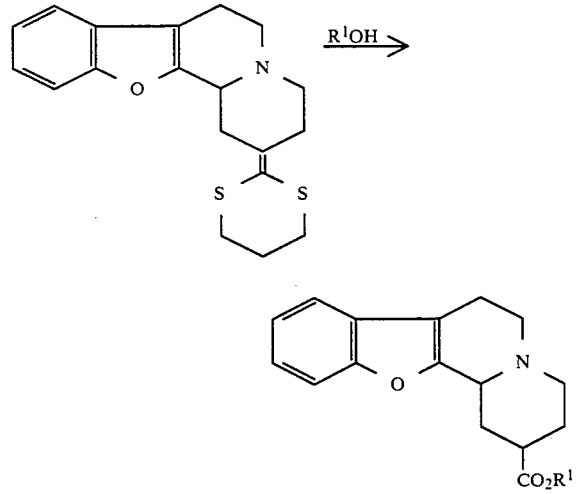

wherein R¹ is —CH₃, —CH₂CH₂CH₃, —CH(CH₃)₂, —CH(CH₃)CH₂CH₃ and —(CH₂)₄CH₃.

EXAMPLE 5

(2RS,12bSR)-2-Acetyl-1,3,4,6,7,12b-hexahydro-2H-benzo[b]furo[2,3-a]quinolizine Hydrochloride 1-Ethylthiotriethylphosphonate (2.34 g; 10.4 mmol) was dissolved in 50 mL of THF and cooled in an acetone-dry ice bath under N₂ gas. To this solution, n-butyl lithium (8.8 mmol) was added dropwise. After stirring for 3 hours, (12bRS)-1,3,4,6,7,12b-hexahydro-2H-benzo[b]furo[2,3-a]quinolizin-2-one (1.93 g; 8 mmol) in 20 mL of THF was added to the solution which then was stirred for 1 hour with cooling, for 1 hour at room temperature, and overnight at 50° C. Water (40 mL) and saturated NH₄Cl solution were added successively to the reaction mixture which was then extracted into ether. The ether layer was washed with saturated NaHCO₃ solution, brine, and water. Evaporation gave an oil. The oil was dissolved in 20 mL of ethanol and to this solution, 20 mL of ethanol saturated with dry HCl gas and 5 drops of H₂O were added with stirring at room temperature. After stirring overnight, the ethanol was evaporated to give a brown residue which was redissolved in ethyl acetate and made basic with dilute NH₄OH. The ethyl acetate layer was separated, washed with H₂O, and dried over K₂CO₃. Evaporation gave a dark oil which was subjected to silica-gel column chromatography. Ethyl acetate eluted the desired product. The free base was converted to the hydrochloride salt with ethanol/HCl, m.p. >260° C.

Employing the procedure substantially as described in Example 5, but substituting for the Wittig reagent and benzo[b]furoquinolizin-2-one used therein the Wittig reagents and arylquinolizin-2-ones described in Table II, there are produced the 2-alkanoyl-arylquiniolizines also described in Table II in accordance with the following reaction scheme:

TABLE II

| Ar | R¹ |
|---|---|
| benzo- | —CH₃ |
| pyridino- | —C₃H₇—n |
| benzo[b]furo- | —C₂H₅ |
| benzo[b]thieno- | —C₄H₉—n |
| thieno- | —CH(CH₃)₂ |
| furo- | —CH₃ |

EXAMPLE 6

(2RS,12bS)-1,3,4,6,7,12b-Hexahydro-2-(1-hydroxyiminoethyl)-2H-benzo[b]furo[2,3-a]quinolizine Hydrochloride Into a mixture of 10 mL of ethanol and 3 mL of pyridine, (2RS,12bSR)-2-Acetyl-1,3,4,6,7,12b-hexahydro-2H-benzo[b]furo[2,3-a]quinolizine (0.4 g; 1.5 mmol) and hydroxylamine hydrochloride (0.1 g; 1.5 mmol) were added. After 2 hours stirring, the product precipitated. The solid was collected by filtration and washed with ethyl acetate several times, m.p. 280° C.

Employing the procedure substantially as described in Example 6, but substituting for the 2-acetyl-benzo[b]furoquinolizine used therein, the 2-alkanoyl-arylquinolizines described in Tables II and III there are produced the oximes described in Table III in accordance with the following reaction scheme:

TABLE III

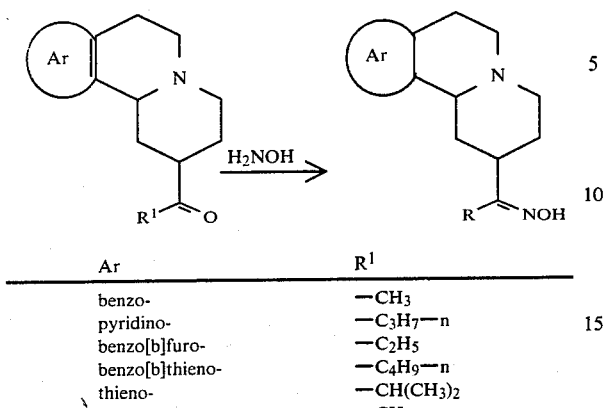

| Ar | R¹ |
|---|---|
| benzo- | —CH₃ |
| pyridino- | —C₃H₇—n |
| benzo[b]furo- | —C₂H₅ |
| benzo[b]thieno- | —C₄H₉—n |
| thieno- | —CH(CH₃)₂ |
| furo- | —CH₃ |

TABLE IV

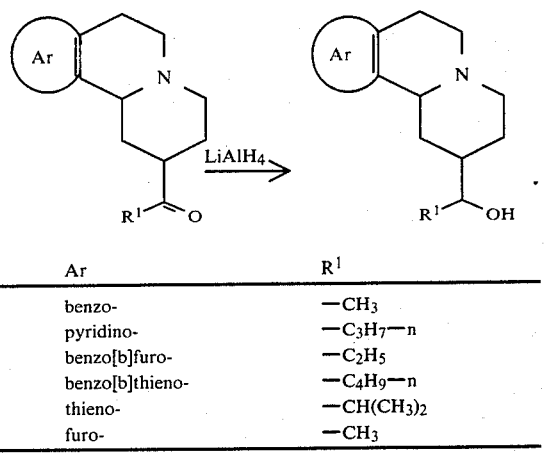

| Ar | R¹ |
|---|---|
| benzo- | —CH₃ |
| pyridino- | —C₃H₇—n |
| benzo[b]furo- | —C₂H₅ |
| benzo[b]thieno- | —C₄H₉—n |
| thieno- | —CH(CH₃)₂ |
| furo- | —CH₃ |

EXAMPLE 7

(2RS,12bSR)-1,3,4,6,7,12b-Hexahydro-2-(1-methoxyiminoethyl)-2H-benzo[b]furo[2,3-a]quinolizine Hydrochloride Methoxyamine hydrochloride (0.17 g; 2.0 mmol) and (2RS,12bSR)-2-Acetyl-1,3,4,6,7,12b-hexahydro-2H-benzo[b]furo[2,3-a]quinolizine (0.45 g; 1.7 mmol) were dissolved in 10 mL of pyridine and stirred at room temperature overnight under N₂ gas. The reaction mixture was poured into 3% NaHCO₃ solution and then extracted into ethyl acetate. The ethyl acetate layer was washed with brine and H₂O, and dried over K₂CO₃. Evaporation of the ethyl acetate gave an oil which was subjected to silica gel column chromatography. A mixture of CH₂Cl₂ and ethyl acetate (4:1) eluted 280 mg of the free base of the product as an oil.

The oil was transformed into the HCl salt in HCl/ethanol. Evaporation of the ethanol gave a white solid which was recrystallized from ethyl acetate/ether to give the product, m.p. 228° C. (d).

EXAMPLE 8

(2RS,12bSR)-1,3,4,6,7,12b-Hexahydro-2-(1-hydroxyethyl)-2H-benzo[b]furo[2,3-a]quinolizine Hydrochloride Into an ether solution of (2RS,12bSR)-2-acetyl-1,3,4,6,7,12b-hexahydro-2H-benzo[b]furo[2,3-a]quinolizine (1.4 g), LiAlH₄ (0.4 g) was added and the mixture was stirred under N₂ overnight. Water, 15% NaOH, and water were added successively. A precipitated solid was filtered off and from the mother liquor the ether layer was separated which was then washed with water, dried over MgSO₄, and evaporated to give the crude alcohol product. The alcohol was subjected to column chromatography and transformed into the HCl salt, recrystallized from methanol/ethyl acetate/ether, to yield 400 mg, m.p. 235° C. (d).

Employing the procedure substantially as described in Example 8 but substituting for the 2-acetyl-benzo[b-]furoquinolizine used therein, the 2-alkanoyl-arylquinolizines described in Tables II and IV, there are produced the 1-hydroxyalkyl derivatives described in Table IV in accordance with the following reaction scheme:

EXAMPLE 9

(2RS,12bSR)-1,3,4,6,7,12b-Hexahydro-2-(1-methyl-1-hydroxyethyl) 2H-benzo[b]furo[2,3-a]quinolizine Hydrochloride Methylmagnesium bromide (1 mmol) was added to a solution of (2RS,12bSR)-2-acetyl-1,3,4,6,7,12b-hexahydro-2H-benzo[b]furo[2,3-a]quinolizine (0.269 g; 1 mmol) in 15 mL ether at 0° C. After 2 hours 20 mL of saturated NH₄Cl solution was added to the reaction mixture. The organic layer was separated and evaporated to a yellow solid which was crystallized from ether. The free base was converted to the hydrochloride salt by treatment with ethanolic HCl to give the product, m.p. 255°–256° C.

Employing the procedure substantially as described in Example 9, but substituting for the methyl magnesium bromide and the 2-acetyl-benzo[b]furoquinolizine used therein, the Grignard reagents and 2-alkanoylarylquinolizines described in Table V, there are produced the tertiary alcohols also described in Table V in accordance with the following reaction scheme:

TABLE V

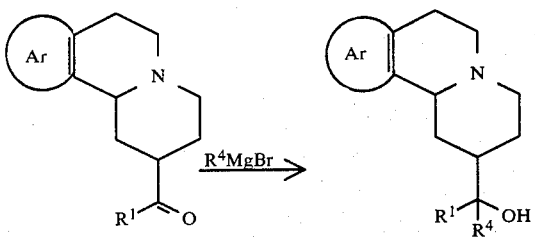

| Ar | R¹ | R⁴ |
|---|---|---|
| benzo- | —CH₃ | —CH₃ |
| pyridino- | —C₃H₇—n | —C₂H₅ |
| benzo[b]furo- | —C₂H₅ | —C₃H₇—n |
| benzo[b]thieno- | —C₄H₉—n | —CH₃ |
| thieno- | —CH(CH₃)₂ | —CH₃ |
| furo- | —CH₃ | —CH₂—CH=CH₂ |

EXAMPLE 10

(2RS,12bSR)-1,3,4,6,7,12b-Hexahydro-2-(1-(2-hydroyethoxy)ethyl) 2H-benzo[b]furo[2,3-a]quinolizine hydrochloride

Step A: Preparation of (2RS,12bSR) Ethyl 1-(1,3,4,6,7,12b hexahydro-2H-benzo[b]furo[2,3-a]quinolizin-2-yl)ethoxyacetate Hydrochloride A solution of (2RS,12bSR)-1,3,4,6,7,12b-hexahydro-2-(1-hydroxyethyl)-2H-benzo[b]furo[2,3-a]quinolizine (0.7 g; 2.7 mmol) in 20 mL of DMF-benzene (1:1) was added to a suspension of NaH (5.4 mmol) in 20 mL of DMF-benzene at 0° C. with stirring. After the subsequent addition of ethyl bromoacetate (0.45 g; 3 mmol), the reaction was stirred at 25° C. for 3 hours. Dilute HCl was added until the reaction mixture was acidic and then NH$_4$OH was added until the mixture was basic. The mixture was extracted with ether. The organic extracts were washed with water, dried over MgSO$_4$, and evaporated to give the product as an oil.

Step B: Preparation of (2RS,12bSR)-1,3,4,6,7,12b-hexahydro-2-(1-(2-hydroxyethyoxy)ethyl)-2H-benzo[b]furo[2,3-a]quinolizine Hydrochloride A solution of the ester obtained in Step A above (0.32 g) and NaBH$_4$ (0.087 g) in 4 mL of t-butanol was heated to reflux. Methanol (0.8 mL) was added over 1 hour. The reaction mixture was cooled and water was added. The solvent was evaporated, and the residue was extracted with ether. The ether extracts were washed with water, dried over MgSO$_4$, and evaporated to give the free base of the product as an oil. The oil was converted to the hydrochloride salt, m.p. 147° C. (dec).

Employing the procedure substantially as described in Example 10, but substituting for the 2-(1-hydroxyethyl)-benzo[b]furoquinolizine used therein, the 2-(1-hydroxyalkyl)-arylquinolizines described in Table VI, there are produced the hydroxyethyl ethers also described in Table VI in accordance with the following reaction scheme:

TABLE VI

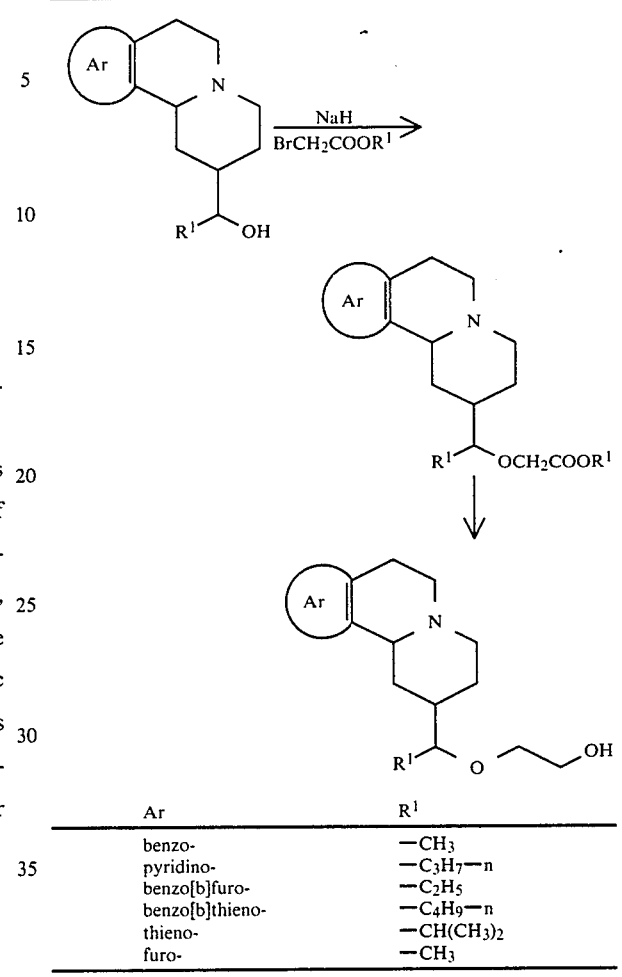

| Ar | R$^1$ |
|---|---|
| benzo- | —CH$_3$ |
| pyridino- | —C$_3$H$_7$—n |
| benzo[b]furo- | —C$_2$H$_5$ |
| benzo[b]thieno- | —C$_4$H$_9$—n |
| thieno- | —CH(CH$_3$)$_2$ |
| furo- | —CH$_3$ |

EXAMPLE 11

(2RS,12bSR)-1,3,4,6,7,12b-hexahydro-2-(1-(2-hydroxyethylamino)ethyl)-2H-benzo[b]furo[2,3-a]quinolizine Dihydrochloride.

A solution of ethanolamine (0.136 g), NaCNBH$_3$ (0.46 g), 5N methanolic HCl (0.15 mL), and (2RS,12bSR)-2-acetyl-1,3,4,6,7,12b hexahydro-2H-benzo[b]furo[2,3-a]quinolizine (0.1 g) in 2 mL of methanol was stirred at 50° C. for 18 hours. The reaction mixture was first made acidic with dilute HCl and then basic with NH$_4$OH. The resulting mixture was extracted with CHCl$_3$. The extracts were washed with water, dried over MgSO$_4$, and evaporated to give the free base of the product as an oil. The oil was converted to the dihydrochloride salt and recrystallized from methanol-ether to give the product, m.p. 250° C.

EXAMPLE 12

(2RS,12bSR)-1,3,4,6,7,12b-Hexahydro-2-(1-methyl-1-(2-hydroxyethoxy)ethyl)-2H-benzo[b]furo[2,3-a]quinolizine Hydrochloride

Step A: Preparation of (2RS,12bSR)-1,3,4,6,7,12b-hexahydro-2-(2-methyl-1,3,-dioxalan-2-yl)-2H-benzo[b]furo[2,3-a]quinolizine A mixture of ethyleneglycol (1 mL), borontrifluoride etherate (1 mL), and (2RS,12bSR)-2-acetyl- 1,3,4,6,7,12b-hexahydro-2H-benzo[b]furo[2,3-a]quinolizine (0.5 g) in 2 mL of CH$_2$Cl$_2$ was stirred at 25° C. for 18 hours in the dark. Water (10 mL) was then added with vigorous stirring. The methylene chloride was evaporated, and the residual aqueous mixture was extracted with ethyl acetate. The organic extract was washed with water, dried over MgSO$_4$, and evaporated. Chromatography over silica gel, eluting with methylene chloride-ethyl acetate, afforded the product as an oil.

Step B: Preparation of (2RS,12bSR)-1,3,4,6,7,12b-hexahydro-2-(1-methyl-1-(2-hydroxyethoxy)ethyl)-2H-benzo[b]furo[2,3 a]quinolizine Hydrochloride The oil (0.4 g) from Step A and methylmagnesium bromide (12.7 mmol) were dissolved in benzene, and the mixture was refluxed for 18 hours. Into the cooled reaction mixture, 20 mL of 25% ammonium acetate was added, and the benzene layer was separated. The organic extracts were washed with water, dried over MgSO$_4$, and evaporated to give an oil. The oil was chromatographed over silica gel, eluting with CH$_2$Cl$_2$/ethyl acetate/ethanol (4:2:1), to afford the free base of the product which was converted into the hydrochloride salt, m.p. 222°–223° C.

Employing the procedure substantially as described in Example 12, but substituting for the 2-acetyl-benzo[b]furoquinolizine and methyl magnesium bromide used therein, the 2-alkanoyl-arylquinolizines and the Grignard reagents described in Table VII, there are produced the hydroxyethoxy compounds, also described in Table VII in accordance with the following reaction scheme:

TABLE VII

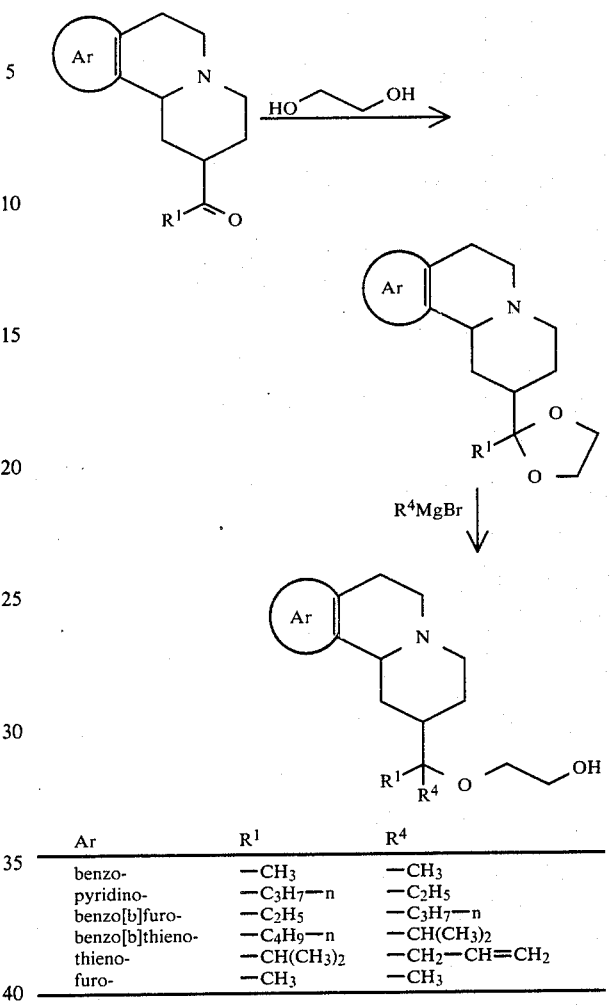

| Ar | R$^1$ | R$^4$ |
|---|---|---|
| benzo- | —CH$_3$ | —CH$_3$ |
| pyridino- | —C$_3$H$_7$—n | —C$_2$H$_5$ |
| benzo[b]furo- | —C$_2$H$_5$ | —C$_3$H$_7$—n |
| benzo[b]thieno- | —C$_4$H$_9$—n | —CH(CH$_3$)$_2$ |
| thieno- | —CH(CH$_3$)$_2$ | —CH$_2$—CH═CH$_2$ |
| furo- | —CH$_3$ | —CH$_3$ |

EXAMPLE 13
(2RS,12bSR)-1,3,4,6,7,12b-Hexahydro-2-(1-(2-hydroxyethylthio)ethenyl)-2H-benzo[b]furo[2,3-a]quinolizine Step A: Preparation of (2RS,12bSR)-1,3,4,6,7,12b-hexahydro-2-(2-methyl-1,3,-oxathiolan-2-yl)-2H-benzo[b]furo[2,3-a]quinolizine A solution of (2RS,12bSR)-2-acetyl-1,3,4,6,7,12b-hexahydro 2H-benzo[b]furo[2,3-a]quinolizine (0.25 g), 2-mercaptoethanol (0.2 mL), and borontrifluoride etherate (0.4 mL) in 5 mL of acetic acid was stirred at 25° C. for 18 hours. The acetic acid was evaporated, and NH$_4$OH was added to the residue. The aqueous mixture was extracted with ethyl acetate. Evaporation of the organic extracts afforded an oil which was chromatographed over silica gel, eluting with methylene chloride-ethyl acetate (1:1) to give 0.25 g of the product as an oil.

Step B: Preparation of (2RS,12bSR)-1,3,4,6,7,12b-hexahydro-2-(1-(2-hydroxyethylthio)ethenyl)-2H-benzo[b]furo[2,3-a]quinolizine Aluminum chloride (0.116 g) was placed in a flask and cooled in an ice bath. Cold ether (2 mL) was added, and the mixture stirred 15 minutes until solution was affected. LiAlH$_4$ (0.01 g) was added in 1 mL of ether.

Fifteen minutes later, the product from Step A (0.23 g) in 2 mL of ether was added, and the ice bath was removed. The reaction mixture was heated at reflux for 2 hours. Water (0.2 mL) was added, followed by 1 mL of 10% $H_2SO_4$. A saturated solution of $NaHCO_3$ was then added until the reaction was basic. The reaction mixture was extracted with ethyl acetate. The extracts were washed with water, dried over $MgSO_4$, and evaporated to afford an oil. The oil was chromatographed over silica gel and then recrystallized to yield 0.022 g of the product, m.p. 116°–117° C.

EXAMPLE 14

(2RS,12bSR)-N-(1,3,4,6,7,12b-Hexahydro-2H-benzo[b]furo[2,3-a]quinolizin-2-yl)methyl-N,N'-trimethylsulfamide Hydrochloride Step A: Preparation of (2RS,12bSR)-1,3,4,6,7,12b-Hexahydro-2-methoxymethylidene-2H-benzo[b]-furo[2,3-a]quinolizine To a cold (0° C.) solution of diisopropylamine (0.22 g; 2.2 mmole) in 6 mL of tetrahydrofuran (THF) was added n-butyl lithium (1 mL of a 2.1 molar solution, 2.1 mmole). After 15 minutes this mixture was added via syringe to a suspension of methoxymethyltriphenylphosphine chloride (0.685 g; 2.0 mmole) in 5 mL of toluene at 0° C., stirred 15 minutes, and then a solution of (12bRS)-1,3,4,6,7,12b-hexahydro-2H-benzo[b]furo[2,3-a]quinolizin-2-one (0.12 g; 0.5 mmole) in 3 mL of toluene was added. After 30 minutes, the reaction mixture was poured into water (50 mL), washed with ether (2×40 mL), the ether washed with brine (40 mL), dried ($Na_2SO_4$), filtered and concentrated. The oily residue was chromatographed (silica, ethyl acetate/hexanes, 1:1) to give 104 mg of a 1:1 mixture of E and Z enol ethers as an oil. Exact mass-calc 269.1416, Found 269.14163.

Step B: Preparation of (2RS,12bSR) and (2SR,12bSR)-1,3,4,6,7,12b-Hexahydro-2H-benzo[b]furo[2,3-a]quinolizine-2-carboxaldehyde The mixture of enol ethers (104 mg; mmole) from Step A was dissolved in 6 mL of 2N HCl, stirred for 4 hours at 25° C., made basic and extracted with methylene chloride (2×40 mL), dried ($Na_2SO_4$), filtered and concentrated to give 60 mg of crude aldehyde a (2:1) mixture of (2RS,12bSR):(2SR,12bSR) aldehydes.

Step C: Preparation of (2RS,12bSR)-1,3,4,6,7,12b-Hexahydro-2-methylaminomethyl-2H-benzo[b]furo[2,3-a]quinolizine To a solution of aldehydes from Step B (0.15 g; 0.56 mmole) in 3 mL of methanol was added methylamine hydrochloride (0.18 g; 2.8 mmol) and sodium cyanoborohydride (0.050 g; 0.78 mmole). After 48 hours at 25° C., the reaction was concentrated to dryness, 5 mL of 6N HCl added, stirred 30 minutes, diluted with 30 mL of water, made basic and extracted with methylene chloride (2×30 mL), dried ($Na_2SO_4$), filtered and concentrated to an oil which was chromatographed (silica, $NH_3$ saturated $CHCl_3$/1% MeOH) to give 65 mg of product.

Step D: Preparation of (2RS,12bSR)-N-(1,3,4,6,7,12b-Hexahydro-2H-benzo[b]furo[2,3-a]quinolizin-2-yl)methyl-N,N'-trimethyl sulfamide Hydrochloride To a solution of the amine from Step C (0.065 g; 0.24 mmole) in b 2 mL of methylene chloride was added 0.050 g (0.48 mmole) of triethylamine and 0.070 g (0.48 mmole) of dimethylsulfamoyl chloride. After 18 hours at 25° C., this was poured into 10 mL of saturated $NaHCO_3$, extracted into methylene chloride (2×20 mL), dried ($Na_2SO_4$) filtered and concentrated to give an oil which was chromatographed (silica, ethyl acetate) to give 0.05 mg of the free base of the product. The HCl.¼$H_2O$ salt was generated in ethyl acetate and ethanolic HCl, m.p. 242°–245° C.

EXAMPLE 15

Pharmaceutical Formulation

| Ingredient | Mg/Capsule |
|---|---|
| (2RS,12bSR)-Methyl (1,3,4,6,7,12b-hexahydro-2H—benzo[b]furo[2,3-a]-quinolizin-2-yl) acetate Hydrochloride | 6 |
| starch | 87 |
| magnesium stearate | 7 |

The active ingredient, starch and magnesium stearate are blended together. The mixture is used to fill hard shell capsules of a suitable size at a fill weight of 100 mg per capsule.

EXAMPLE 16

| Ingredient | Mg/Capsule |
|---|---|
| (2RS,12bSR)-1,3,4,6,7,12b-Hexahydro-2-(1-methyl-1-hydroxyethyl)-2H—benzo[b]furo[2,3-a]quinolizine Hydrochloride | 6 |
| starch | 87 |
| magnesium stearate | 7 |

What is claimed is:

1. A compound of structural formula:

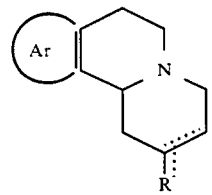

or a pharmaceutically acceptable salt thereof wherein Ar represents an aromatic group selected from X,Y-benzo[b]furo-, X,Y-benzo[b]thieno-, and; wherein X and Y are independently:

(1) hydrogen,
(2) halo,
(3) hydroxy,
(4) $C_{1-3}$alkoxy, or
(5) $C_{1-6}$alkyl;

R is (1)

wherein $R^1$ is hydrogen or $C_{1-5}$ alkyl, either straight or branched chain;

(2)

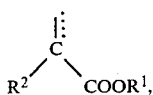

wherein $R^2$ is
(a) hydrogen,
(b) $C_{1-5}$ alkyl, or
(c) $C_{1-5}$ alkylidene;

(3)

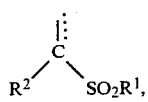

(4)

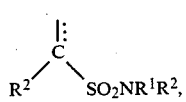

wherein $R^1$ and $R^2$ can be joined together to form pyrrolidine or piperidine;

(5)

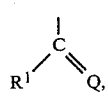

wherein Q is
(a) O, or
(b) $N\!-\!OR^1$;

(6)

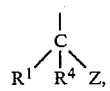

wherein Z is
(a) $-OR^3$ or $-SR^3$
(b) $-NR^2R^3$, wherein $R^3$ is (i) H,
(ii) $C_{1-5}$ alkyl, unsubstituted or substituted with
  (1) $-OH$
  (2) $-COOR^1$,
  (3) $-SO_2R^2$,
  (4) $-N(R^2)SO_2R^2$,
(iii) $-COOR^2$,
(iv) $-SO_2R^2$,
(v) $SO_2NR^1R^2$;

$R^4$ is
(a) $C_{1-5}$ alkyl, or
(b) $C_{1-5}$ alkylidene; and
the broken lines represent possible double bonds.

2. The compound of claim 1, wherein Ar is benzo[b]furo—.

3. The compound of claim 2, wherein R is $CH_2CO_2R^1$, $CH_3CHCO_2R^1$, $R^1\!-\!C\!=\!NOR^3$, $R^1(R^4)C\!-\!OH$, $R^1CHO(CH_2)_2OH$, or $R^1(R^4)CO(CH_2)_2OH$ wherein $R^1$, $R^3$ and $R^4$ are independently $C_{1-5}$ alkyl or H.

4. The compound of claim 3, wherein $R^1$, and $R^4$ are methyl and $R^3$ is H.

5. A pharmaceutical composition for the treatment of depression, comprising a pharmaceutical carrier and an effective amount of the compound of claim 1.

6. The composition of claim 5 wherein the Ar is benzo[b]furo—.

7. The composition of claim 6, wherein R is $-CH_2CO_2R^1$, $CH_3CHCO_2R^1$, $R^1\!-\!C\!=\!NOR^3$, $R^1(R^4)C\!-\!OH$, $R^1CH\!-\!O(CH_2)_2OH$ or $R^1(R^4)C\!-\!O(CH_2)_2OH$ wherein $R^1$, $R^3$ and $R^4$ are independently $C_{1-5}$alkyl or H.

8. The composition of claim 7 wherein $R^1$ and $R^4$ are methyl and $R^3$ is H.

9. A method of treating depression which comprises the administration to a patient in need of such treatment of an effective amount of a compound as described in claim 1.

10. The method of claim 9 wherein Ar is benzo[b]furo—.

11. The method of claim 10, wherein R is $-CH_2CO_2R^1$, $CH_3CHCO_2R^1$, $R^1\!-\!C\!=\!NOR^3$, $R^1(R^4)\!-\!C\!-\!OH$, $R^1CHO(CH_2)_2OH$, or $R^1(R^4)C\!-\!O(CH_2)_2OH$ wherein $R^1$, $R^3$ and $R^4$ are indepenently $C_{1-5}$alkyl or H.

12. The method of claim 11, wherein $R^1$ and $R^4$ are methyl and $R^3$ is H.

* * * * *